(12) United States Patent
Reumers et al.

(10) Patent No.: US 10,697,882 B2
(45) Date of Patent: Jun. 30, 2020

(54) METHOD AND DEVICE FOR DRUG SCREENING

(71) Applicant: IMEC VZW, Leuven (BE)

(72) Inventors: Veerle Reumers, Putte (BE); Dries Braeken, Leuven (BE); Geert Vanmeerbeeck, Keerbergen (BE); Richard Stahl, Rotselaar (BE); Andy Lambrechts, Herent (BE)

(73) Assignee: IMEC VZW, Leuven (BE)

( * ) Notice: Subject to any disclaimer, the term of this patent is extended or adjusted under 35 U.S.C. 154(b) by 106 days.

(21) Appl. No.: 15/129,267

(22) PCT Filed: Apr. 3, 2015

(86) PCT No.: PCT/EP2015/097017
§ 371 (c)(1),
(2) Date: Sep. 26, 2016

(87) PCT Pub. No.: WO2015/150589
PCT Pub. Date: Oct. 8, 2015

(65) Prior Publication Data
US 2017/0115201 A1    Apr. 27, 2017

(30) Foreign Application Priority Data
Apr. 3, 2014 (EP) .................................. 14163422

(51) Int. Cl.
*G01N 33/483* (2006.01)
*G01N 15/10* (2006.01)
(Continued)

(52) U.S. Cl.
CPC ..... *G01N 15/1031* (2013.01); *G01N 15/1434* (2013.01); *G01N 15/1468* (2013.01);
(Continued)

(58) Field of Classification Search
CPC .................................................. G01N 33/4836
See application file for complete search history.

(56) References Cited

U.S. PATENT DOCUMENTS

| 7,160,687 B1* | 1/2007 | Kapur | B01L 3/5027 356/300 |
| 2002/0028480 A1* | 3/2002 | Maher | G01N 33/5008 435/40 |
| 2010/0178692 A1* | 7/2010 | Yasuda | G01N 33/5061 435/288.7 |

FOREIGN PATENT DOCUMENTS

| EP | 2 657 792 A1 | 10/2013 |
| EP | 2 657 793 A1 | 10/2013 |

(Continued)

OTHER PUBLICATIONS

Lee et al., "Field-portable reflection and transmission microscopy based on lensless holography", 2011, Biomedical Optics Express, vol. 2 No. ( pp. 2721-2730. (Year: 2011).*
PCT International Search Report and Written Opinion, PCT International Application No. PCT/EP2015/097017, dated Jun. 25, 2015, 14 pages.
(Continued)

*Primary Examiner* — Jonathan M Hurst
(74) *Attorney, Agent, or Firm* — McDonnell Boehnen Hulbert & Berghoff LLP (57) ABSTRACT

The present disclosure relates to devices and methods configured to perform drug screening on cells. At least one embodiment relates to a lens-free device for performing drug screening on cells. The lens-free device includes a substrate having a surface. The lens-free device also includes a light source positioned to illuminate the cells, when present, on the substrate surface with a light wave. The lens-free device further includes a sensor positioned to detect an optical signal caused by illuminating the cells. The substrate surface includes a microelectrode array for sensing an electrophysiological signal from the cells.

17 Claims, 8 Drawing Sheets

(51) Int. Cl.
- G01N 21/47 (2006.01)
- G03H 1/04 (2006.01)
- G01N 15/14 (2006.01)
- G01N 21/45 (2006.01)
- G01N 21/17 (2006.01)
- G01N 33/50 (2006.01)
- G03H 1/00 (2006.01)
- G01N 15/00 (2006.01)

(52) U.S. Cl.
CPC ......... G01N 21/1717 (2013.01); G01N 21/45 (2013.01); G01N 21/4788 (2013.01); G01N 33/4836 (2013.01); G01N 33/5044 (2013.01); G03H 1/0005 (2013.01); G03H 1/0402 (2013.01); G03H 1/0443 (2013.01); G03H 1/0465 (2013.01); G01N 21/453 (2013.01); G01N 2015/0065 (2013.01); G01N 2015/1006 (2013.01); G01N 2015/1454 (2013.01); G01N 2021/1721 (2013.01); G01N 2021/1738 (2013.01); G01N 2021/1765 (2013.01); G01N 2201/062 (2013.01); G01N 2201/06113 (2013.01); G01N 2500/10 (2013.01); G03H 2001/005 (2013.01); G03H 2001/0033 (2013.01); G03H 2001/0447 (2013.01); G03H 2001/0469 (2013.01); G03H 2001/0471 (2013.01); G03H 2222/22 (2013.01); G03H 2226/11 (2013.01)

(56) References Cited

FOREIGN PATENT DOCUMENTS

| | | |
|---|---|---|
| EP | 3 040 750 A1 | 7/2016 |
| WO | 2010/148252 A1 | 12/2010 |
| WO | 2016/124677 A1 | 8/2016 |

OTHER PUBLICATIONS

Kim, Sang Bok et al., "A Cell-Based Biosensor for Real-Time Detection of Cardiotoxicity Using Lensfree Imaging", Lab on a Chip, vol. 11, No. 10, Apr. 11, 2011, pp. 1801-1807.

Greenbaum, Alon et al., "Imaging Without Lenses: Achievements and Remaining Challenges of Wide-Field On-Chip Microscopy", Nature Methods, vol. 9, No. 9, Sep. 2012, pp. 889-895.

Gurkan, Umut Atakan et al., Miniaturized Lensless Imaging Systems for Cell and Microorganisms Visualization in Point-Of-Care Testing, Biotechnology Journal, vol. 6, No. 2, Feb. 7, 2011, pp. 138-149.

Natarajan, A. et al., "Microelectrode Array Recordings of Cardiac Action Potentials as High Throughput Method to Evaluate Pesticide Toxicity", Toxicology in Vitro, vol. 20, No. 3, Sep. 29, 2005, pp. 375-381.

Cui, Xiquan et al., "Lensless High-Resolution On-Chip Optofluidic Microscopes for Caenorhabditis Elegans and Cell Imaging", PNAS, vol. 105, No. 31, Aug. 5, 2008, pp. 10670-10675.

Lee, Myungjun et al., "Field-Portable Reflection and Transmission Microscopy Based on Lensless Holography", Biomedical Optics Express, vol. 2, No. 9, Sep. 1, 2011, pp. 2721-2730.

\* cited by examiner

METHOD AND DEVICE FOR DRUG SCREENING

CROSS-REFERENCE TO RELATED APPLICATION

The present application is a national stage entry of PCT/EP2015/097017 filed Apr. 3, 2015, which claims priority to European Patent Application No. 14163422.0 filed on Apr. 3, 2014, the contents of each of which are hereby incorporated by reference.

FIELD OF THE INVENTION

The disclosure relates to in-vitro pharmacological drug screening. In particular, the disclosure relates to the screening of drugs for cardiac toxicity.

BACKGROUND TO THE INVENTION

During drug development it is important to predict the safety and efficiency of candidate drugs as early as possible in the process to reduce the risks for patients and to reduce costs. For example, cardiotoxicity is one of the primary reasons why new drugs are withdrawn during preclinical or full clinical trials and even after FDA approval.

The paper "A cell-based biosensor for real-time detection of cardiotoxicity using lens-free imaging" by Kim et al. describes a sensor which measures the effects of two different drugs, isoprenaline and doxorubicin, on the beating rate and beat-to-beat variations of ESC-derived cardiomyocytes. The system only allows detection of optical information related to the physical contraction of cardiomyocytes. Other parameters such as electrophysiological signals of cells cannot be recorded.

There is a need for techniques and devices which are compact and increase the accuracy of drug screening.

SUMMARY OF THE INVENTION

In a first aspect, a lens-free device for performing drug screening on cells is presented comprising: a substrate having a surface; a light source positioned to illuminate the cells, when present, on the substrate surface with a light wave; a sensor positioned to detect an optical signal caused by illuminating the cells; characterized in that: the substrate surface comprises a microelectrode array for sensing an electrophysiological signal from the cells.

According to an example embodiment, the substrate surface is a reflective surface for reflecting the light wave, and the sensor is positioned to detect the reflected light wave.

According to an example embodiment, the lens-free device further comprises a beam-splitting device positioned in between the substrate and the sensor and configured to direct the light wave towards the cells and further configured to transmit the reflected light wave.

According to an example embodiment, the substrate is transparent, at least for the optical signal, and the sensor is positioned to detect the optical signal through the substrate.

According to an example embodiment, the substrate surface comprises patterns for controlling the growth of cells.

According to an example embodiment, the lens-free device further comprises a processing unit, electrically connected to the sensor and to the microelectrode array, configured to correlate the detected optical signal and the sensed electrophysiological signals.

According to an example embodiment, the sensor comprises a through-hole and the radiation source is positioned to emit the light wave through the through-hole.

According to an example embodiment, the light source is configured to generate different light waves, each light wave having a different wavelength range and causing an optical signal with a different wavelength range, and the sensor is adapted for detecting the different optical signals. The light source may consist of a single light emitting element capable of generating light waves in different wavelength ranges, or it may comprise a plurality of light emitting elements, each capable of generating light waves of at least one wavelength range, at least two light emitting elements of the plurality of light emitting elements being capable of generating light waves of different wavelength ranges.

According to an example embodiment, the substrate comprises a fluidics system configured to provide a candidate drug to cells on the substrate surface for contacting cells on the substrate surface with the candidate drug.

According to an example embodiment, the fluidics system is configured to provide different candidate drugs to cells at different locations on the substrate surface for contacting different cells on the substrate surface with a different candidate drug.

In a second aspect, a method for performing drug screening on cells is presented, comprising: providing cells; contacting cells with a candidate drug; illuminating the cells with a light wave; detecting and recording an optical signal caused by illuminating the cells; characterized in that: the method further comprises detecting and recording an electrophysiological signal of the cells, simultaneously or in parallel with the detection and recording of the optical signal; and correlating the recorded optical signal with the recorded electrophysiological signals for determining influence of the candidate drug on the cells.

According to an example embodiment, the method further comprises reconstructing an image representation of the cells using the recorded optical signal, and correlating the image representation with the recorded electrophysiological signal.

According to an example embodiment, illuminating the cells, detecting and recording the optical signal, detecting and recording the electrophysiological signal and correlating the optical signal with the recorded electrophysiological signal is repeated at least once using a light wave with a different wavelength range.

According to an example embodiment, the method further comprises counting the cells using the correlated signals.

The lens-free device described in the first aspect may be used to perform the method as described in the second aspect.

DETAILED DESCRIPTION OF THE INVENTION

Throughout the description reference is made to a "lens-free" device. This may refer to a lens-free imaging device. A "lens-free" device may be a device wherein no lenses are used to perform imaging of an object.

Throughout the description reference is made to an "optical signal" or "optical signals". These signals are the result of interference between diffracted light caused by illuminating an object and the light wave used to illuminate the object. The optical signal can also be defined as an "interference pattern".

Throughout the description reference is made to "electro-mechanical window" of biological cells like for instance cardiac cells. In pharmacology, for instance cardiovascular pharmacology, electrical and mechanical events can be distinguished, and the phrase "electro-mechanical window" describes the temporal difference between these events.

It some embodiments, a multimodal feed-out device is provided for the analysis of cells, wherein different parameters of cells can be analyzed at the same time. Further, a sensing device may be provided for optically detecting cells and simultaneously recording bio-signals from those cells, as this improves the accuracy of drug screening. In example embodiments, an accurate drug screening device is provided for determining the toxicity of a candidate drug on biological cells, e.g. cardiac cells, by detecting physical contraction of the biological cells, e.g. cardiac cells, and simultaneously detecting electrical signals from contracting biological cells, e.g. cardiac cells.

In a first aspect, a lens-free device for performing drug screening on cells is presented. The device is capable of simultaneously recording optical and electrophysiological signals of cells. The device comprises a substrate with a surface to hold, grow or provide cells on. The substrate may be a semiconductor substrate, e.g. a silicon substrate. The substrate may be a thinned substrate, e.g. etched silicon. The substrate may be a micro-chip. A light source is positioned and configured to illuminate cells present on the substrate with a light wave. Hereto, one or more light emitting elements may be placed remote to the location where the drug screening is to take place, and light waves generated by the light emitting elements may be brought to the location where the drug screening is to take place, by an optical guiding element, for instance an optical fiber. The light source may then for instance be an end of the optical fiber. Alternatively, the one or more light emitting elements may be provided at the location where the drug screening is to take place, and the light source is formed directly by the one or more light emitting elements.

The light source is suitable for performing lens-free imaging. For example, the light source may be a coherent light source, e.g. a laser. The light source may be an optical fiber coupled laser module. To increase compactness and reduce costs, a light system comprising at least one LED may be used. According to an example embodiment, the light source comprises a pinhole for imparting a spatial coherence to a light wave generated by a non-coherent light source, e.g. a LED. A sensor is positioned and configured to detect an optical signal caused by illuminating the cells. The optical signal is the result from interference between diffracted light from illuminated cells and the original light wave. This technique is known as inline digital holography, which allows holograms of cells to be recorded by the sensor. Hence, the sensor is positioned such that holograms of cells can be recorded when the cells are illuminated. The sensor may be an image sensor, e.g. a CMOS image sensor. The substrate comprises a micro-electrode array (MEA) for sensing electrophysiological signals from cells. The micro-electrode array may also be used for actuating cells. The MEA may be located at the surface of the substrate. The microelectrode array may be at least partially embedded in the substrate. The MEA may be a passive MEA (only sensing of cells) for measuring impedance of cells present on the surface of the substrate. Such a MEA may be used to detect electrophysical signals of cells, such as for instance contraction of cells, by measuring electrical signals, e.g. its impedance, and to reduce power consumption. The MEA may be an active MEA (sensing of cells and optionally also actuation of cells) suitable for stimulating cells and sensing electrophysiological signals from cells. In some embodiments, the use of an active MEA allows reproducible measurements wherein the MEA may be used to stimulate one more cells in a specific manner to induce a specific event in the cells. For example, one or more cells may be stimulated to induce a contraction in the cells. By stimulating the cells sequentially in a specific and similar manner, a series of measurements of the same event induced by the stimulation may be performed on the cells.

According to an example embodiment, the light source may be a photonic integrated circuit as described in EP14200424, including any of its embodiments. Such a photonic integrated circuit comprises an optical waveguide and one or more light couplers coupled to the optical waveguide, for coupling light out of the optical waveguide towards the biological material under test. According to an example embodiment, the light source may be a light source as described in EP15154087, including any of its embodiments. Such a light source comprises a plurality of light emitters which conjointly create a quasi-planar light wavefront for performing lens-free imaging on the biological material under test.

The substrate surface may be a substantially flat surface wherein the electrodes are located in the substrate surface, at the same level as the substrate surface. Thus, the electrodes are integrated in the substrate surface and form a part of that surface while still allowing direct contact with cells present on that substrate surface. Such a configuration allows a substantially flat substrate surface to be used to sense cells and optionally also to actuate cells.

Alternatively, the electrodes may be formed by protrusions on the substrate surface, such as pillars or nanorods present on the substrate surface. These protrusions, e.g. pillars or nanorods, may be positioned perpendicular on the substrate surface. The height of a protrusion, e.g. pillar or a nanorod, may be between 300 nm and 2 micrometer, the area of the top surface of a protrusion, e.g. pillar, may be between 1.3 and 15 micrometer$^2$. The pillars or nanorods may be metal pillars or nanorods. In particular embodiments, the pillars or nanorods may be reflective structures. Alternatively, the pillars or nanorods may be fabricated from a transparent conductive material, e.g. a transparent conductive oxide such as indium titanium oxide.

The electrodes of the MEA, whether integrated in the surface or positioned on the substrate surface, may be electrically connected to electronic circuitry, e.g. CMOS circuitry, located in the substrate via conductive wires, e.g. metal wires. The conductive wiring, e.g. metal wiring, may be embedded completely in the substrate, positioned such that it does not hinder optical or electrical measurements. The electronic circuitry may be configured to transmit electrical signals via the metal wires to each electrode individually. The electronic circuitry may be configured to receive or record electrical signals from each electrode individually. Thus, each electrode may be addressable individually for recording purposes on a single cell level. On top thereof, each electrode may be addressable individually for purpose of stimulation of cells. Further, the electronic circuitry may be configured to simultaneously sense, and optionally also actuate, one or more groups of electrodes. This allows sensing, and optionally actuation, of groups of cells in contact with those groups of electrodes. For this purpose, the electronic circuitry may comprise multiplexing and/or de-multiplexing circuitry.

In some embodiments, optical information and electrophysiological information of cells can be registered at the same time. Optical information of cells can be used to extract different parameters from the cells. For example, when biological cells such as cardiac cells are under test, different biological parameters may be extracted, for instance cardiac contraction parameters such as contraction frequency, contraction strength, signal propagation through the tissue, duration of the contraction, relaxation duration, total contraction duration, contraction peak, relaxation peak, total contraction peak. Each of these parameters may be related to a specific electrophysiological signal resulting in a very accurate drug screening. Thus, by monitoring different parameters of cells at the same time, e.g. monitoring contraction of a cell by optical inspection and electrophysiological signals of that cell by electronic inspection, at the same time, the effect of a candidate drug on the cell can be determined with high accuracy. For example, when performing drug screening on a biological cell such as a cardiac cell, it can be determined to which electrophysiological signal a contraction of the cell is related. This is in contrast to alternate systems which only allow recording of one parameter of a cell at a time. Thus, in accordance with example embodiments, it can be accurately determined how cells respond to a candidate drug. The integration of multiple readout systems in a single device yields more information from the same cells thereby allowing a correlation to be performed on different datasets (optical signal+electrophysiological signal), extracted at the same moment in time. In some embodiments, manipulation of the cells, e.g. moving the cells from one detection site to another one, is not necessary to extract different information or different parameters from cells. This leads to a better and more accurate drug screening application. Further, as multiple parameters may be monitored in parallel, time to perform the drug screening may be reduced.

The example embodiments as presented in this disclosure also allow an assessment of the electromechanical window of biological cells, such as for instance cardiac cells, by using the difference between the electrophysiological and optical information of the biological cells, e.g. cardiac cells. In alternate systems, in contrast, the accurate determination of that parameter is not possible because electrophysiological and optical information cannot be measured simultaneously.

According to an example embodiment, the surface of the substrate is a reflective surface suitable for reflecting the optical signal caused by illuminating cells. Thus, the reflective surface is configured for reflecting the optical signal which is the result from interference between diffracted light from illuminated cells and the original light wave used to illuminate the cells. For visible light, the reflective surface may comprise a mirror, e.g. a polished front-surface mirror, for example comprising a conductive layer, such as a gold layer, arranged on top of the substrate. The reflective surface may be or comprise a metal layer, a TiN layer, or a silicon surface. In particular embodiments, the reflective surface may be provided in between the electrodes and the wiring. On top of that, also the electrodes themselves and the wiring may help in reflecting the impinging radiation.

In this embodiment where the substrate surface is a reflective surface and the lens-free device is arranged for operating in reflective mode, the sensor is positioned to record the reflected optical signal from illuminated cells. The reflective surface may allow the device to operate in reflection mode which reduces the size of the device and increases compactness. As discussed above, the substrate surface may be a substantially flat surface wherein electrodes are part of the substrate surface, positioned at the same level as the substrate surface, still allowing direct contact with cells on the substrate surface. This flat surface may comprise electrodes and a reflective material present in between the electrodes. The reflective material may for instance be silicon or a metal. A substantially flat surface has improved reflection properties which may improve the quality of the detection of the reflected optical signal from illuminated cells.

Figure 1:
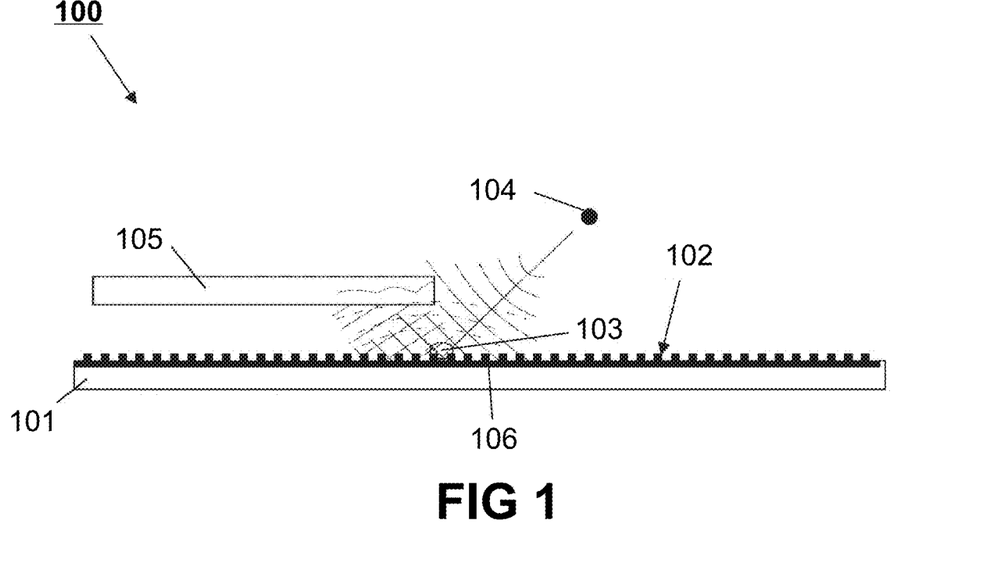
FIG. 1 illustrates lens-free device for drug screening of cells, according to an example embodiment.

FIG. 1 illustrates an example embodiment wherein the surface 102 of the substrate 101 is a reflective surface. A light source 104 is positioned to allow a light wave generated by the light source 104 to reach one or more cells 103 present at, e.g. on and in close contact with, the reflective surface 102, without any objects blocking its transmission path. When the light wave reaches the cell 103, diffraction of the light wave on the cell occurs, resulting in diffracted light. The diffracted light is reflected by the reflective surface 102 of the substrate 101. A part of the original light wave which does not diffract on the cell is also reflected by the reflective surface. The reflected diffracted light and the reflected original light wave interfere resulting in an optical signal. The optical signal is recorded by a sensor 105 which is positioned parallel or substantially parallel to the substrate 101 and adjacent to the surface at the side of the reflective surface 102, thereby allowing recording of the optical signal. The substrate 101 comprises a micro-electrode array which is used to record electrophysiological signals from cells 103 present on the surface 102 of the substrate 101. The micro-electrode array comprises a plurality of electrodes 106, which may be implemented integrated in the surface 102 or positioned on the substrate surface 102, for instance as pillars or rods. While illuminating cells 103 and recording optical signals caused by illumination of the cells 103, electrophysiological signals of the cells can be recorded simultaneously.

Figure 2:
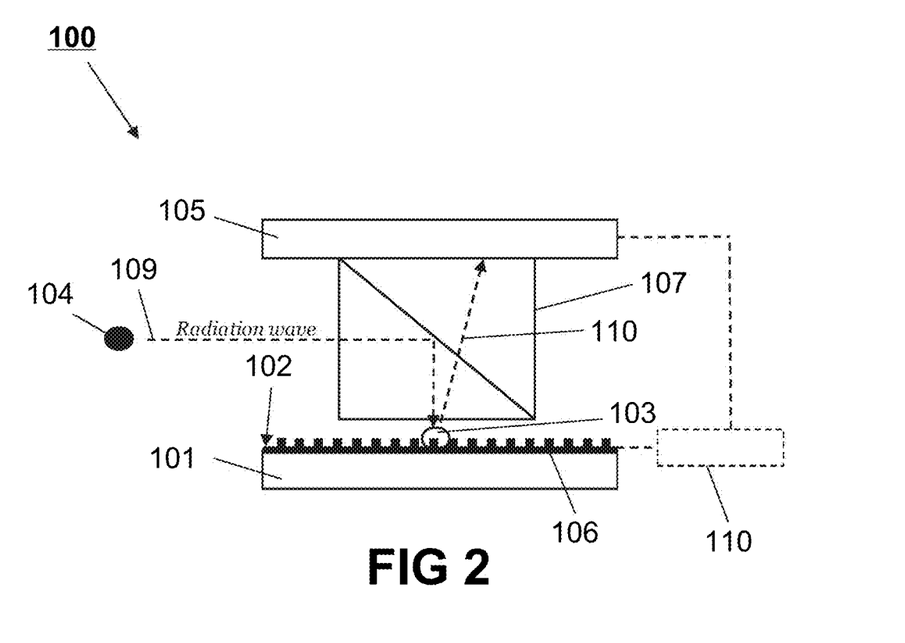
FIG. 2 illustrates lens-free device for drug screening of cells, according to an example embodiment.

According to an example embodiment, the lens-free device 100 comprises a beam-splitting device configured to direct a light wave generated by the light source towards cells 103, when present on, e.g. in close contact with, the substrate surface 102. FIG. 2 illustrates such an embodiment. The beam-splitting device 107 may be positioned in between the substrate 101 and the sensor 105. The substrate 101 and the sensor 105 are positioned parallel or substantially parallel to each other, wherein the sensing side of the sensor faces the reflective surface 102 of the substrate 101 on which cells 103 are held, provided or growing. The beam-splitting device 107 is positioned to redirect a light wave generated by the light source 104 onto cells 103 which are present on the surface 102 of the substrate 101. The beam-splitting device 107 may redirect the light wave emanating from the light source 104, illustrated as arrow 109, thereby achieving perpendicular or substantially perpendicular illumination of cells 103 present on the substrate surface 102. Efficient detection of optical signals from cells with the image sensor 105 parallel or substantially parallel to the surface 102 may be achieved and compactness of the device may be increased. The beam-splitting device 107 is further configured to allow light waves reflected by the reflective surface 102 of the substrate 101 to transmit through the beam-splitting device 107 and to be received by the sensor 105, illustrated as arrow 110. In some embodiments, efficient illumination of cells 103 can be achieved. In addition, compactness of the complete device 100 can be further increased as the light wave generated by the light source 104 may enter the beam splitting device 107 substantially parallel with the substrate surface 102 and the sensor's 105 sensing surface. Also in this embodiment, the substrate 101 comprises a micro-electrode array for recording electrophysiological signals from cells 103 present on the surface 102 of the substrate 101. The micro-electrode array may be as discussed above, for instance with respect to FIG. 1. While illuminating cells 103 and recording optical signals caused by illumination of the cells 103, electrophysiological signals of the cells can be recorded simultaneously.

Figure 3:
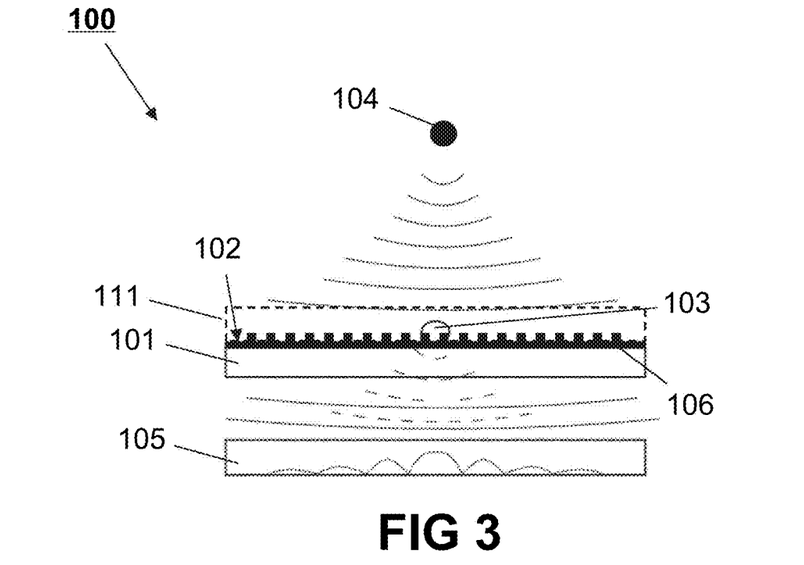
FIG. 3 illustrates lens-free device for drug screening of cells, according to an example embodiment.

According to an example embodiment, the substrate 102 is fabricated from a transparent material, e.g. silicon oxide (glass) or a transparent polymer. The sensor 105 is positioned to record optical signals from cells present on the substrate surface 102. In this embodiment, the sensor 105 and the light source 104 are provided at different sides of the substrate 101, with the light source 104 being located at that side of the substrate 101 where the surface 102 is provided with electrodes 106, and the sensor 105 being located at the side of the substrate 101 opposite thereto. In this embodiment, as discussed above, the electrodes 106 (which may for instance be implemented as pillars, nanorods positioned on the substrate surface 102 or electrodes integrated in the substrate surface 102) of the MEA may be fabricated from a transparent conductive material which allows transmission of optical signals from cells. To allow optical signals to propagate through the substrate 101, the electronic circuitry of the MEA may be positioned at one of the sides of the substrate to keep the electronic circuitry from blocking the transmission path of optical signals in the substrate. Alternatively, the substrate 101 comprising the MEA may be thinned, thereby allowing propagation of light through the substrate 101. FIG. 3 illustrates such an embodiment. A sensor 105 is positioned substantially parallel with a substrate 101. A cell 103 is positioned on a surface 102 of the substrate 101. The substrate surface 102 faces away from the sensor 105. The sensing side of the sensor 105 faces the substrate 101. The substrate 101 comprises a micro-electrode array for sensing cells and optionally for actuating cells. A light source 104 is positioned to illuminate the substrate surface 102. The substrate 101 is fabricated from a transparent material that allows transmission of the light wave generated by the light source 104 and diffracted light from the illuminated cell 103. In certain embodiments, optical information of cells detected in transmission mode (through the substrate) provides enhanced image quality, comparable to image quality of traditional microscopy images. Also this embodiment allows to simultaneously detect optical and electrophysical signals from cells 103.

According to example embodiments, the lens-free device 100 according to any embodiments, for instance, but not limited thereto, the devices 100 as described with respect to FIG. 1 to FIG. 4, may furthermore comprise a processing unit 110 which is electrically connected to the sensor 105 and to the micro-electrode array comprising the plurality of electrodes 106. The processing unit 110 is configured to combine the detected optical signals from cells 103 and the electrophysiological signals of the cells 103. In particular embodiments, the processing unit 110 may be configured to correlate the detected optical signals from cells 103 and the electrophysiological signals of the cells 103. A goal of correlating the detected optical and electrophysical signals is to align the datasets, so that data relating to a same event on a cell, e.g. influence of a particular dose of a drug under particular circumstances including environmental circumstances like temperature, pH etc., can be taken into account. By performing a correlation between the two datasets (optical+electrophysiological), the effect of a candidate drug on the cells 103 under test can be more accurately determined. Whereas signals of similar cell events recorded at different moments in time (for instance subsequently) are difficult to correlate due to e.g. manipulation of the cell under test or e.g. the difficulty in reproducing the same event in the cell, in some embodiments allow optical and electrophysiological signals of cells to be obtained simultaneously.

Figure 4:
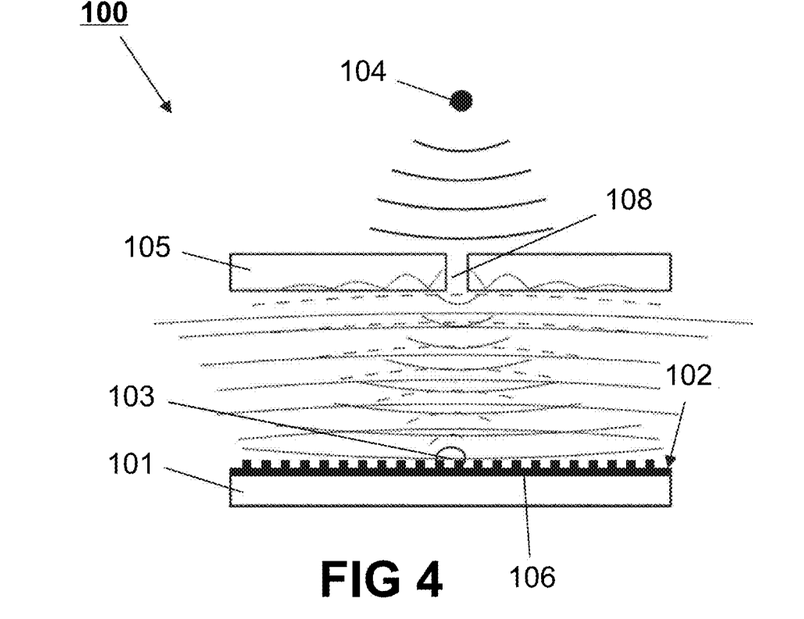
FIG. 4 illustrates lens-free device for drug screening of cells, according to an example embodiment.

According to an example embodiment, configured to operate in reflective mode, the sensor 105 comprises a through-hole 108. The light source 104 is positioned to emit a light wave through the through-hole 108, onto the substrate surface 102. The through hole is an aperture perforating the sensor 105 to allow a light wave to pass through the through-hole. In particular embodiments, not illustrated in the drawings, the light source may be located inside the through-hole. The through-hole may be optically coupled to the light source for imparting a spatial coherence to the light wave generated by the light source. Thus, the through-hole may function as a pinhole for illuminating cells 103 with spatially coherent light. In some embodiments, the sensor 105 can be placed close to and parallel to the substrate 101. FIG. 4 illustrates such an embodiment. A sensor 105 and a substrate 101 are positioned substantially parallel to each other. The substrate surface 102 used for holding, growing or providing cells on faces the sensing side of the sensor 105. The sensor 105 comprises a through-hole 108. A light source 104 is positioned to generate a light wave through the through-hole 108 and to illuminate the surface 102 (and as a consequence also cells when present) of the substrate 101.

According to an example embodiment, the surface 102 of the substrate 101 which is used to hold, provide or grow cells on is a patterned surface adapted for mimicking in vivo organization through structured cell growth. For example, the surface 102 may be patterned to induce a structured growth of cells 103, for instance of cardiac cells. In this way, the grown cells may be made comparable to the structure of a human organ, for instance a human heart. The pattern may for instance comprise or consist of parallel lines, or any other suitable pattern as known in the art. In some embodiments, by mimicking the actual structure of, for instance, the heart, a realistic measurement may be performed because the cells 103 on the substrate surface 102 are a realistic representation of the structure of the heart, including how it contracts and responds to external stimuli. The surface may comprise structures that control the growth of cells 103 on the surface 102. For example, the structures may control the direction of growth of cells 103 on the surface 102. This may be achieved by providing structuring, e.g. grooves, in the substrate surface 102. According to a specific embodiment, the electrodes 106 implemented as protrusions, for instance pillars or nanorods, of the micro-electrode array are positioned and spaced from each other to induce a structured growth of cells 103 on the substrate surface 102. The electrodes 106, e.g. pillars, may be positioned in groups or in one or more rows spaced from each other to stimulate the cells 103 to grow in a specific direction. According to an example embodiment, to control the growth of cells 103 on the substrate surface 102, the substrate surface 102 may be provided, on selected areas, with a modification material for chemically or biologically modifying the surface so as to influence, e.g. allow or repel, growth of cells. This modification material may be applied, for instance, by printing. The printed surface comprises different areas or zones, selected to provide a particular pre-defined pattern, wherein each area or zone may be configured to differently influence, e.g. allow or repel, growth of cells. The different areas of the printed substrate surface may comprise a material, e.g. a biological material, that influences e.g. allows or repels, growth of cells. By controlling the direction of growth of cells 103, the conduction direction of cells can be controlled which simplifies post-processing of optical and electrophysiological signals and increases the relevance of the signals. In certain embodiments, software algorithms may be used for analyzing signals from cells 103 may be simplified because conduction motion vectors of cells are more aligned. The use of simpler algorithms may allow faster processing of data from cells. The conduction of contraction of cells 103 is perpendicular to the contraction direction of the cells. Thus, by controlling the design of the structures on the patterned surface, the motion vectors of cells under test and the conduction of contraction of cells can be controlled or predicted. In some embodiments, the knowledge of how cells contract and in which direction contraction propagates simplifies the measuring of electrophysiological signals.

Figure 5A:
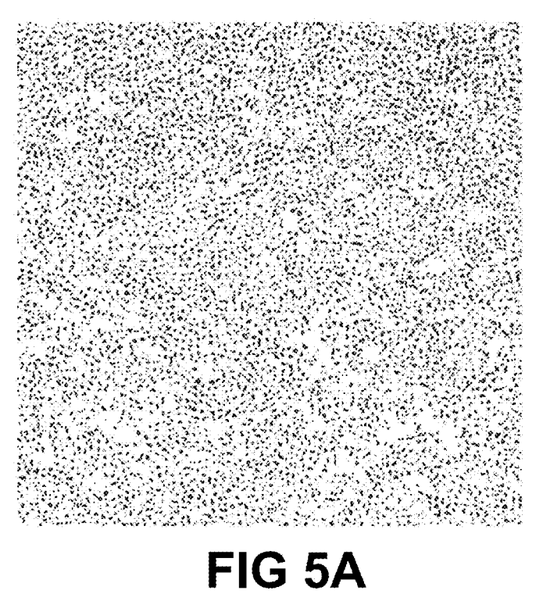
FIG. 5A illustrates the growth of cells on an non-patterned surface, according to an example embodiment.
Figure 5B:
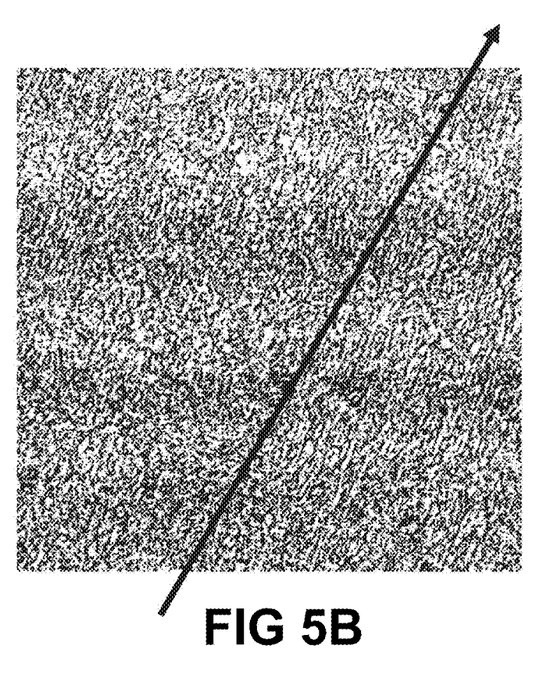
FIG. 5B illustrates the growth of cells on a patterned surface, according to an example embodiment.

FIG. 5A and FIG. 5B illustrate the difference in cell growth between a non-patterned surface (FIG. 5A) and a patterned surface (FIG. 5B). The arrow in FIG. 5B indicates the direction of growth of cells on the substrate surface 102.

According to an example embodiment, the light source 104 is configured to generate different light waves, each light wave having a different wavelength range. The light source may be adapted to emit light waves with different wavelength ranges. The light source may consist of a single light emitting element capable of generating light waves in different wavelength ranges, or it may comprise a plurality of light emitting elements, each capable of generating light waves of at least one wavelength range, at least two light emitting elements of the plurality of light emitting elements being capable of generating light waves of different wavelength ranges. The sensor 105 may be adapted for detecting light waves with the different wavelength ranges. For example, the sensor may be a multi-spectral or a hyperspectral image sensor configured to detect optical signals from cells with different wavelength ranges. In certain embodiments, cells 103 under test may be illuminated using light waves with different wavelength ranges to determine information of different parts of the cell. The optical signals from illuminated cells with different wavelength ranges can be used to analyze the effect of a drug on a specific part of the cell under test, e.g. the part of the cell responsible for contraction. This may allow a more accurate and better drug screening to be done. Further, light waves with different wavelength ranges may be used to retrieve phase information which can be used to solve the twin image problem occurring in lens-free imaging applications. By doing so, image quality can be increased resulting in a more accurate drug screening.

According to an example embodiment, the device comprises a fluidic system fluidically coupled to the surface 102 of the substrate 101 for administering a candidate drug to cells 103, when present, on the substrate surface 102. The fluidic system may have an inlet and an outlet for providing and exiting a solution comprising the candidate drug.

According to an example embodiment, the substrate comprises a fluidics system 111, e.g. a fluidics or micro-fluidics layer embedded in or on the substrate, which is adapted to provide a candidate drug to one or more locations of the substrate surface for contacting cells when present on that surface with the candidate drug. Such fluidics system 111 is illustrated, as an example only, in the embodiment of FIG. 3, but this is not intended to be limiting. A fluidics system may be used in any lens free device 100 according to example embodiments, for instance, but not limited thereto, the devices 100 as described with respect to FIG. 1 to FIG. 4.

In accordance with example embodiments, the fluidics system 111 may include a conventional fluidics system, such as for instance one or more microfluidic channels provided in a microfluidic substrate, such as a transparent microfluidic substrate, such as for instance a glass substrate or a PDMS (polydimethylsiloxaan) substrate. Such fluidics system 111 may be provided on top of the substrate surface 102 such that cells 103 may be provided inside the one or more microfluidics channels. The microfluidic channels may be filled with fluid, also called the cell medium. The fluid may contain elements to keep the cells 103 in good health. The fluid in the one or more microfluidic channels may be static (no flow) or dynamic (flow). In case of the fluid being in flow, cells 103 may be conducted by the flow, towards and away from detections sites where optical and electrophysical signals are detected. In some embodiments, lens free imaging in the presence of a fluidics system 111 is enabled. The transparent microfluidics substrate, like a glass substrate or a PDMS substrate, proves not to influence the optical measurement results.

According to a specific embodiment, the fluidics system 111 is adapted to provide different candidate drugs to different locations of the substrate surface 102 for contacting different cells 103, when present on the substrate surface 102, with a different candidate drug. For this purpose, the fluidics system 111 may comprise a plurality of fluidic channels, valves and pumps, embedded in the substrate, and configured for distributing different candidate drugs to different locations of the substrate surface. The valves and pumps, which might obstruct the optical path of the light wave for illuminating the cells 103 or the optical signal caused by the illumination of the cells 103, may be positioned outside the area used for imaging.

According to a specific embodiment, the substrate surface 102 comprises a plurality of wells suitable for providing, holding or growing cells on, each well being fluidically connected to a fluidic channel of the fluidic system 111. Each well may be used to analyze the effects of a different drug on the cells 103 in that well. In some embodiments, all wells on the substrate surface 102 may be analyzed simultaneously as 1) the lens-free imaging capability of the device 100 provides a large field of view and as 2) electrophysiological signals of cells 103 may be sensed and recorded simultaneously. Such simultaneous analysis may allow different experiments with different candidate drugs to be performed at the same time. This increases the throughput of the system and reduces the time to perform the drug screening.

According to an example embodiment, the cells under test are biological cells. In a particular embodiment, the cells are cardiac cells, neurons or any other adherent cell. Some embodiments may be used for cardiac cells as simultaneous detection of electrophysiological signals and cardiac contraction is possible, thereby allowing a correlation on different types of signals from cells to be performed. Further, this may allow a more accurate and better drug screening to be done.

Figure 6:
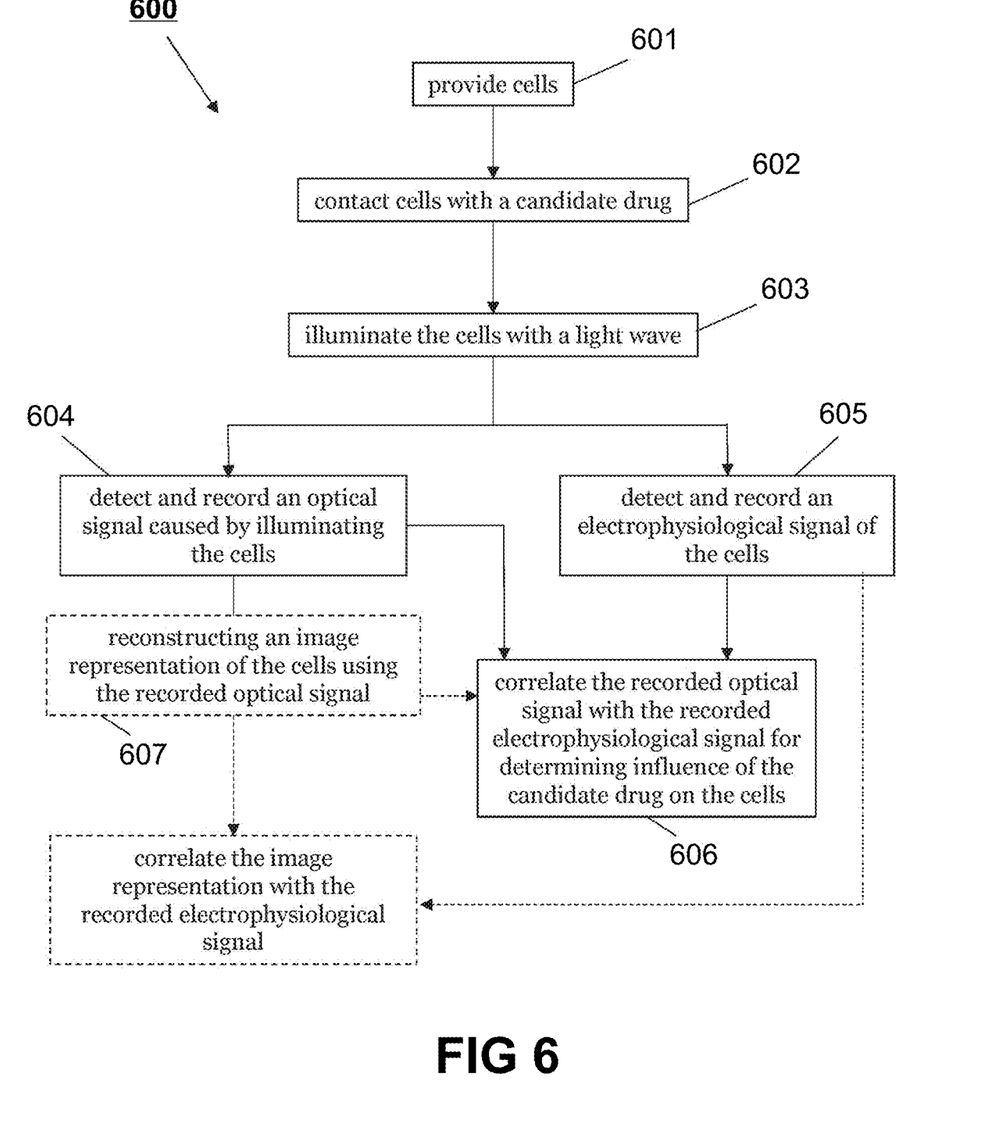
FIG. 6 illustrates a flowchart for performing drug screening on cells, according to an example embodiment.

In a second aspect, a method 600 for performing drug screening on cells 103 is presented. The method 600 is also suitable for assessing the electromechanical window of the cells 103 such as for instance, but not limited thereto, cardiac cells. The method 600 comprises the steps of providing 601 the cells and contacting 602 the cells 103 with a candidate drug, e.g. by providing a solution comprising the candidate drug on the cells 103. Thereafter, the cells 103 are illuminated 603 with a light wave, for instance emanating from a light source 104. During illumination, the light wave diffracts on the cells 103 giving rise to diffracted light. The diffracted light interferes with the original light wave resulting in an optical signal which is detected 604 and recorded. While detecting 604 and recording the optical signal, electrophysiological signals of the cells are detected 605 and recorded in parallel. After the detection 604, 605 and recording of the optical signal and the electrophysiological signal, a correlation 606 between the optical signal and the electrophysiological signal may be performed to determine the influence of the candidate drug on the cells 103. This is illustrated in the flowchart of FIG. 6. The method may be implemented using a device 100 as described in any of the embodiments of the first aspect wherein 1) cells 103 are provided 601 on the substrate surface 102, 2) the cells 103 on the substrate surface 102 are illuminated 603 using the light source 104 and wherein 3) an optical signal and electrophysiological signals of cells are simultaneously detected 604, 605 by the sensor 105 and the micro-electrode array, respectively.

According to an example embodiment, the method may further comprise reconstructing 607 an image representation of the cells 103 using the recorded optical signal. The reconstructed image representation may provide extra information on e.g. the morphology of the cells 103. From the reconstructed image representation more information can be extracted on e.g. the viability status of the cell. This may provide a direct way of checking the viability status of the cell 103, compared to alternate techniques which use indirect ways to check the viability status, e.g. by checking the level of an analyte in a cell. The reconstructed image representation may be correlated with the recorded electrophysiological signal. The reconstructed image representation may be used to extract different parameters from a cell 103 wherein each parameter may be correlated with the recorded electrophysiological signal of that cell. For example, when cardiac cells are under test, cardiac contraction parameters may be extracted such as contraction frequency, contraction strength, signal propagation through the tissue, duration of the contraction. Each parameter may be related to a specific electrophysiological signal. Some embodiments allow images with a quality comparable to microscopy images to be retrieved without sacrificing the large field of view.

Figure 7:
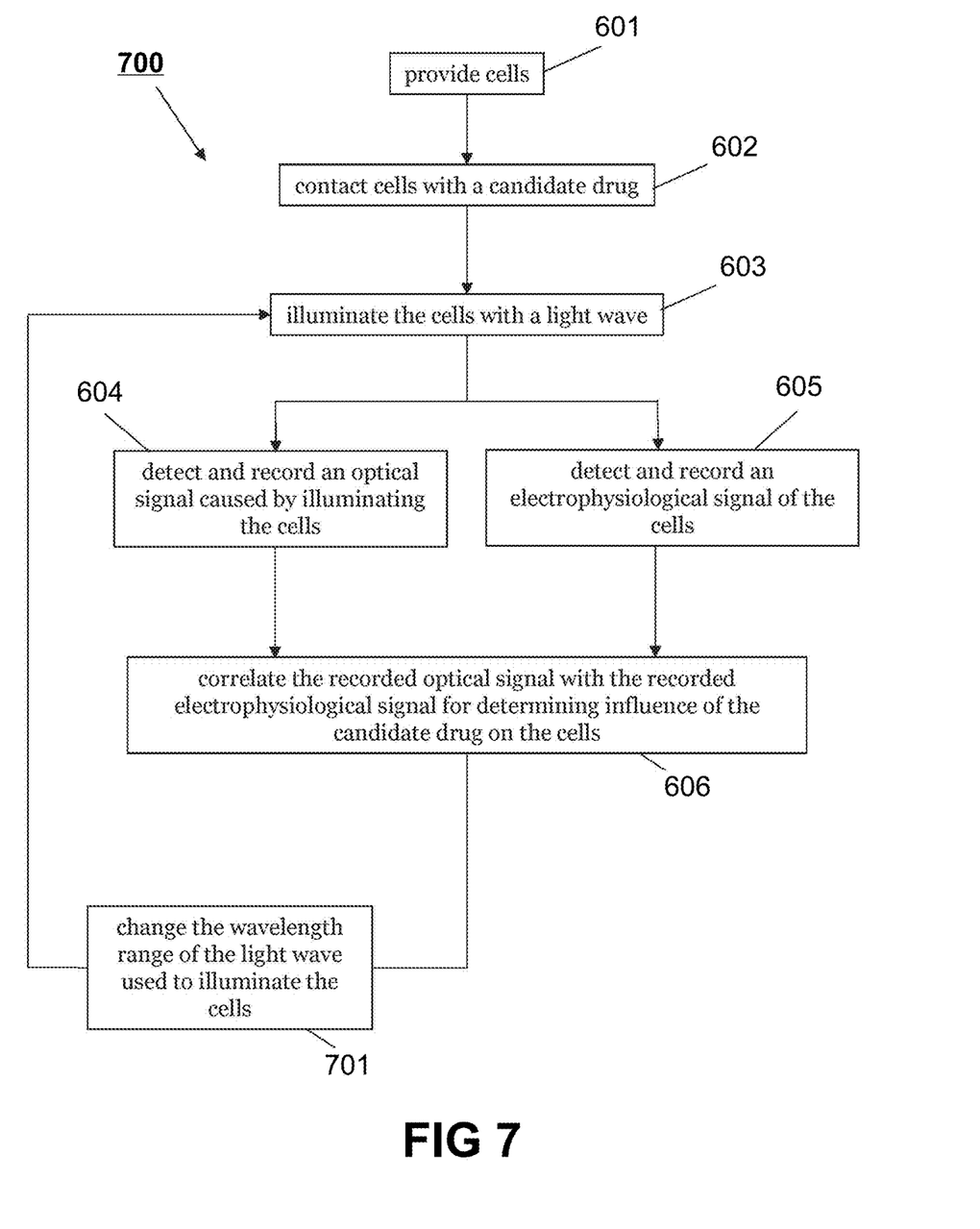
FIG. 7 illustrates a flowchart for performing drug screening on cells using light waves with different wavelength ranges, according to an example embodiment.

According to an example embodiment, light waves with different wavelength ranges are used to illuminate the cells 103 sequentially. This is illustrated in the flowchart 700 of FIG. 7. In any sequence, cells are illuminated 603 with a light wave with a specific wavelength range, optical and electrophysiological signals are detected 604, 605 and recorded and the signals are correlated 606. In between two sequences, the wavelength range of the light wave used to illuminate the cells is changed 701; such that in different sequences, cells are illuminated with a light wave with a different wavelength range, optical and electrophysiological signals are detected and recorded and the signals are correlated. The different datasets (optical signal+electrophysiological signal) for each wavelength range may be correlated to determine influence of the candidate drug on the cells 103. As described above, using light waves with different wavelength ranges may also reveal specific information on the structure of the cell 103, e.g. different parts of the cell.

According to an example embodiment, not illustrated in the drawings, the method further comprises counting the cells using the correlated signals. The simultaneous recording of optical signals and electrophysiological signals from cells and the correlation of both type of signals can be used to perform a counting of cells. Some embodiments, due to correlating, may provide an increased accuracy of the counting. Further, as simultaneous detection of optical and electrophysiological signals is possible, time needed to perform the counting can be reduced.

According to an example embodiment, the method for performing drug screening may further comprise actuating the cell 103 for inducing an event in the cell. For example, the cell may be actuated to induce a contraction. The actuating may be performed while detecting and recording optical and electrophysiological signals. In accordance with example embodiments, the electrodes 106 of the microelectrode array may be used for actuating the cells 103.

Example embodiments were evaluated for the visualization of cardiac cells on a micro-structured reflective surface 102. An experimental setup consisted of a beam splitter 107 placed between a sensor 105 and a sample 103, and a laser 104 which illuminated the setup from the side (such as illustrated in FIG. 2). The coherent light from the light source 104 was directed onto the sample surface 102 through the beam splitter 107 and the incoming light was substantially perpendicular to the sample 103. The reflected light was then recorded by the sensor 105 and was further analyzed by focusing through reconstruction or by the detection of contractions. Samples were initially measured in dry conditions as well as under refractive index matching liquid and cell culture medium. Samples consisted of either silicon samples containing pattern samples with ridges consisting of 800 nm width, 500 nm height and 1600 nm spacing or MEA arrays. These samples were plated with cardiac cells extracted from 2 day old neonatal rats.

Figure 8A:
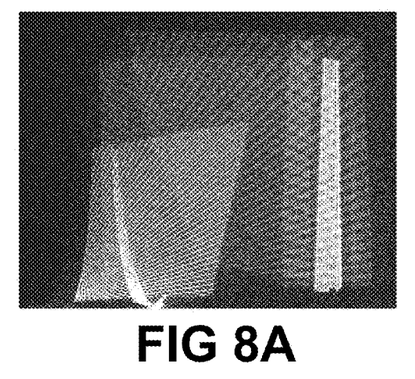
FIG. 8A illustrates optical signals captured during experiments, according to an example embodiment.
Figure 8B:
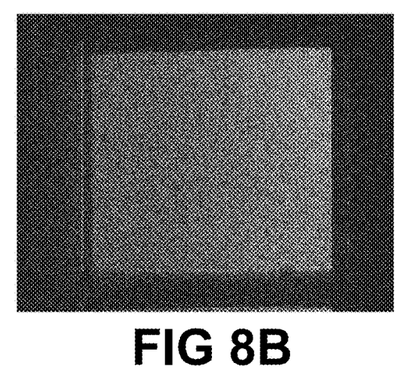
FIG. 8B illustrates optical signals captured during experiments, according to an example embodiment.
Figure 8C:
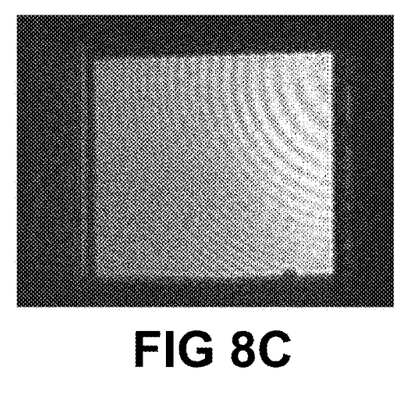
FIG. 8C illustrates the reconstruction of optical signals captured during experiments, according to an example embodiment.
Figure 9A:
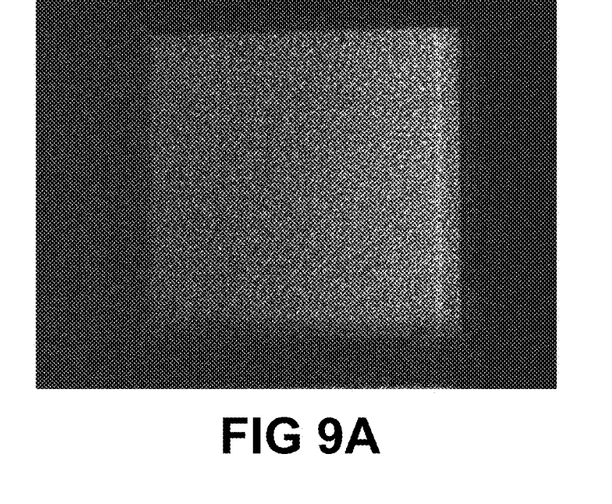
FIG. 9A illustrates optical signals from monolayers of cardiac cells, according to an example embodiment.
Figure 9B:
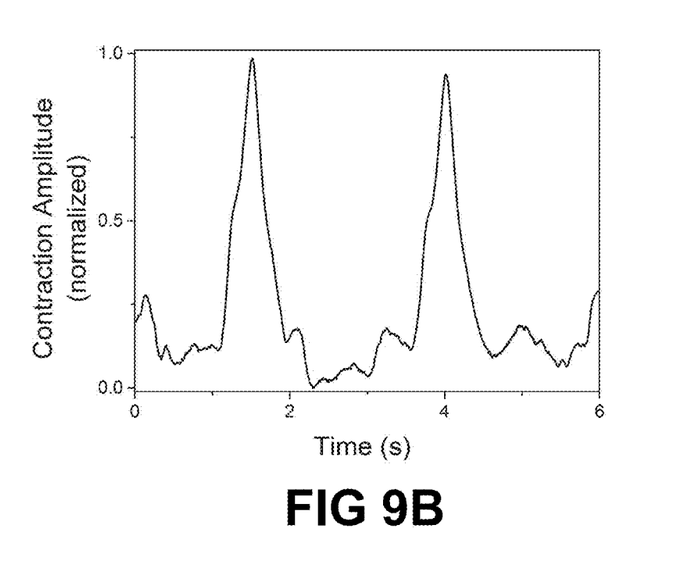
FIG. 9B is a graph setting out the contraction of cells, according to an example embodiment.

Patterned silicon oxide substrates were visualized through reflective lens free imaging at a rate of 100 frames per second and the obtained holograms showed that the field-of-view was limited by the size of the beam splitters 107 and enclosed by interference fringes from the beam splitter edges. If the patterned substrate was visualized in air, a complex pattern of multiple reflections was detected (FIG. 8A) which was not present if the sample was measured in a refractive index matching liquid (FIG. 8B). Furthermore, low density of fixated cells was detected directly on the hologram (FIG. 8B), which was confirmed by reconstruction (FIG. 8C). The complex pattern of multiple reflections was also not detected in samples containing monolayers of cardiac cells (FIG. 9A) and spontaneous contractions of clusters of cells were detectable after further processing (FIG. 9B).

Figure 10A:
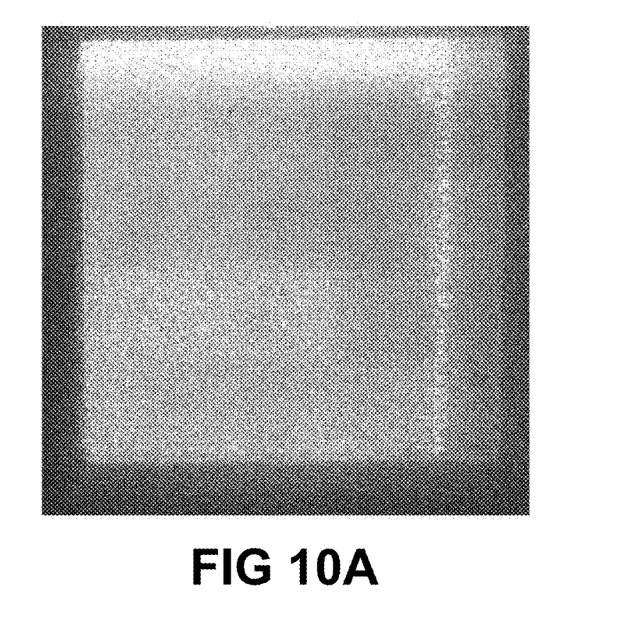
FIG. 10A illustrates optical signals captured during experiments, according to an example embodiment.
Figure 10B:
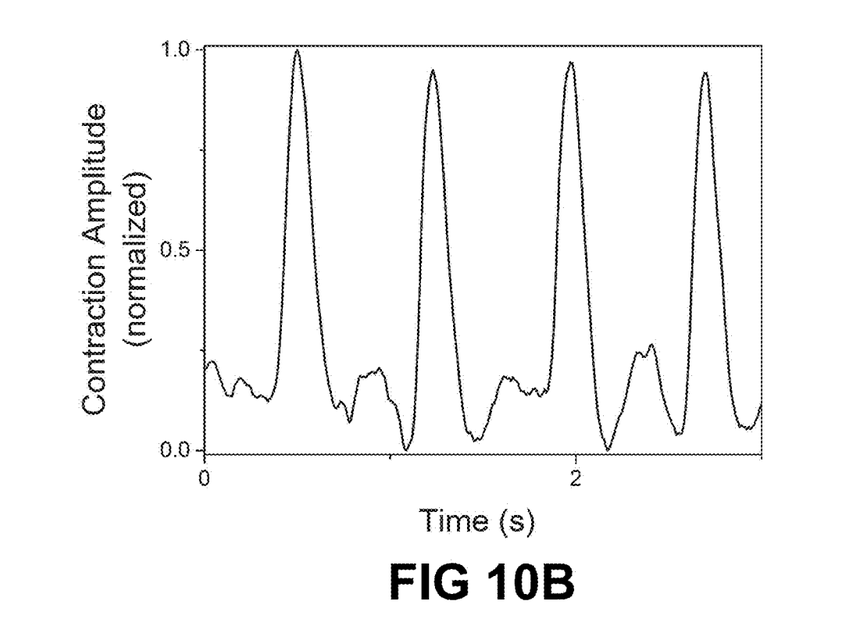
FIG. 10B is a graph setting out the contraction of cells, according to an example embodiment.

The imaging system detected the contraction of cardiac cells of a substrate consisting of a MEA array. The MEA chip was plated with a monolayer of postnatal cardiomyocytes and the obtained holograms showed more complex interference fringes as a result of the MEA topography (FIG. 10A). Nevertheless, the beating of cardiac cells could be measured (FIG. 10B) and the laser intensities did not influence simultaneous electrophysiological measurements.

The invention claimed is:

1. A lens-free device for performing drug screening on cells, comprising:
   a substrate having a reflective surface, wherein the reflective substrate surface comprises a microelectrode array including a plurality of electrodes and wiring for sensing an electrophysiological signal from the cells, wherein the plurality of electrodes are integrated in the reflective substrate surface such that the plurality of electrodes are at the same level as the reflective substrate surface, and wherein the reflective substrate surface comprises a mirror provided in between the plurality of electrodes and the wiring;
   a light source positioned to illuminate the cells, when present, on the reflective substrate surface with a light wave;
   a sensor positioned to detect a light wave reflected off of the reflective substrate surface to thereby detect an optical signal caused by illuminating the cells; and
   a processing unit, electrically connected to the sensor and to the microelectrode array, configured to correlate the detected optical signal and the sensed electrophysiological signal such that data relating to a same event on at least one of the cells is identifiable.

2. The lens-free device according to claim 1, wherein the reflective substrate surface is flat.

3. The lens-free device according to claim 1, further comprising a beam-splitting device positioned in between the substrate and the sensor and configured to direct the light wave towards the cells and further configured to transmit the light wave reflected off of the reflective substrate surface.

4. The lens-free device according to claim 1, wherein the sensor comprises a through-hole, and wherein the light source is positioned to emit the light wave through the through-hole.

5. The lens-free device according to claim 1, wherein the reflective substrate surface comprises patterns for controlling growth of the cells.

6. The lens-free device according to claim 1, wherein each electrode in the microelectrode array is individually addressable in order to sense the electrophysiological signal of a respective cell and in order to stimulate the respective cell.

7. The lens-free device according to claim 1, wherein the light source is configured to generate different light waves, each light wave having a different wavelength range and causing an optical signal with a different wavelength range to determine information about different parts of the cells, and wherein the sensor is adapted for detecting the optical signals with the different wavelength ranges.

8. The lens-free device according to claim 1, wherein the substrate comprises a fluidics system configured to provide a candidate drug to the cells on the reflective substrate surface, and wherein the fluidics system comprises a fluidics layer embedded in the substrate.

9. The lens-free device according to claim 8, wherein the fluidics system is configured to provide different candidate drugs to cells at different locations of the reflective substrate surface.

10. A method for performing drug screening on cells, comprising:
    providing the cells on a substrate having a reflective surface, wherein the reflective substrate surface comprises a microelectrode array including a plurality of electrodes and wiring for sensing an electrophysiological signal from the cells, wherein the plurality of electrodes are integrated in the reflective substrate surface such that the plurality of electrodes are at the same level as the reflective substrate surface, and wherein the reflective substrate surface comprises a mirror provided in between the plurality of electrodes and the wiring;
    contacting the cells with a candidate drug;
    illuminating the cells with a light wave;
    detecting and recording, via a sensor positioned to detect the light wave reflected off of the reflective substrate surface, an optical signal caused by illuminating the cells;
    detecting and recording, via the microelectrode array of the reflective substrate surface, an electrophysiological signal of the cells, simultaneously with the detection and recording of the optical signal; and
    correlating, via a processing unit electrically connected to the sensor and to the microelectrode array, the recorded optical signal with the recorded electrophysiological signal for determining influence of the candidate drug on the cells.

11. The method according to claim 10, further comprising reconstructing an image representation of the cells using the recorded optical signal, and correlating the image representation with the recorded electrophysiological signal.

12. The method according to claim 10, wherein illuminating the cells, detecting and recording the optical signal, detecting and recording the electrophysiological signal and correlating the recorded optical signal with the recorded electrophysiological signal is repeated at least once using a light wave with a different wavelength range.

13. The method according to claim 10, further comprising counting the cells using the correlated recorded optical signal and recorded electrophysiological signal.

14. The method according to claim 10, further comprising:
    directing the light wave, by a beam-splitting device, towards the cells; and
    transmitting the reflected light wave, by the beam-splitting device.

15. The method according to claim 10, further comprising:
    emitting, through a through-hole defined within the sensor, the light wave.

16. The method according to claim 10, further comprising controlling growth of the cells by a substrate surface comprising patterns.

17. A method for performing drug screening on cardiac cells, comprising:
- providing the cardiac cells on a substrate having a reflective surface, wherein the reflective substrate surface comprises a microelectrode array including a plurality of electrodes and wiring for sensing an electrophysiological signal from the cells, wherein the plurality of electrodes are integrated in the reflective substrate surface such that the plurality of electrodes are at the same level as the reflective substrate surface, and wherein the reflective substrate surface comprises a mirror provided in between the plurality of electrodes and the wiring;
- contacting the cardiac cells with a candidate drug;
- illuminating the cardiac cells with a light wave;
- detecting and recording, via a sensor positioned to detect the light wave reflected off of the reflective substrate surface, an optical signal caused by illuminating the cardiac cells;
- detecting and recording, via the microelectrode array of the reflective substrate surface, an electrophysiological signal of the cardiac cells, simultaneously with the detection and recording of the optical signal; and
- correlating, via a processing unit electrically connected to the sensor and to the microelectrode array, the recorded optical signal with the recorded electrophysiological signal for determining influence of the candidate drug on the cardiac cells.

* * * * *